(12) United States Patent
Kanesaka

(10) Patent No.: US 6,458,098 B1
(45) Date of Patent: Oct. 1, 2002

(54) VASCULAR THERAPY DEVICE

(76) Inventor: Nozomu Kanesaka, 81 Greenwoods Rd., Old Tappan, NJ (US) 07675

( * ) Notice: Subject to any disclaimer, the term of this patent is extended or adjusted under 35 U.S.C. 154(b) by 0 days.

(21) Appl. No.: 09/527,820

(22) Filed: Mar. 17, 2000

(51) Int. Cl.$^7$ .................. A61M 25/10; A61B 18/00
(52) U.S. Cl. .............. 604/101.05; 604/96.01; 604/114; 604/912; 606/194; 607/101
(58) Field of Search .......... 604/96.01, 101.01, 604/101.05, 103.07, 114, 509, 912, 915, 919; 606/194; 607/101

(56) References Cited

U.S. PATENT DOCUMENTS

| | | | | |
|---|---|---|---|---|
| 4,924,863 A | * | 5/1990 | Sterzer | 606/27 |
| 5,057,106 A | * | 10/1991 | Kasevich et al. | 600/549 |
| 5,071,425 A | * | 12/1991 | Gifford et al. | 156/294 |
| 5,199,951 A | * | 4/1993 | Spears | 604/113 |
| 5,295,962 A | * | 3/1994 | Crocker et al. | 604/101.02 |
| 5,464,395 A | * | 11/1995 | Faxon et al. | 604/103.02 |
| 5,470,352 A | * | 11/1995 | Rappaport | 606/194 |
| 5,618,266 A | * | 4/1997 | Liprie | 600/3 |
| 5,916,194 A | * | 6/1999 | Jacobsen et al. | 604/524 |
| 6,217,554 B1 | * | 4/2001 | Green | 604/164.01 |

* cited by examiner

*Primary Examiner*—Michael Powell Buiz
*Assistant Examiner*—Ramesh Krishnamurthy
(74) *Attorney, Agent, or Firm*—Kanesaka & Takeuchi

(57) ABSTRACT

A vascular therapy device is used for treatment, such as injecting or applying medicine, to a lumen or body cavity without surgical treatment. The vascular therapy device includes an elongated shaft, an inflatable balloon attached to a side portion of a distal end portion of the shaft, a first path provided in the shaft and communicating with an inside of the balloon to inflate and deflate the balloon, and a second path provided inside the shaft and extending from a proximal end portion to the distal end portion of the shaft. The second path has an outlet at the distal end portion. When the balloon is inflated, a part of the distal end portion is biased to contact a wall where the shaft is inserted. Thus, when the balloon is inflated, the outlet faces and substantially contacts the wall to thereby provide a treatment through the second path and outlet.

14 Claims, 6 Drawing Sheets

VASCULAR THERAPY DEVICE

BACKGROUND OF THE INVENTION AND RELATED ART STATEMENT

The present invention relates to a vascular therapy device for treatment at an area in and around a body cavity or blood vessel.

Angioplasty has become an acceptable way to treat many types of vascular diseases, and widely used for opening stenosis in the coronary arteries. The most widely used form of angioplasty is PTCA (Percutaneous Transluminal Coronary Angioplasty), wherein a dilation catheter which has an inflatable balloon at a distal end is used. Typically, the balloon catheter is guided through a vascular system by using fluoroscopy until the uninflated balloon is positioned at a desired location, such as the stenosis in the blood vessel. Then, the balloon is inflated by supplying a fluid through an inflation path to stretch and open the artery.

Various techniques and apparatuses suitable for vascular treatment and PTCA have been developed. However, there is no device for directly treating a weakened or diseased portion of the vascular system or the area adjacent thereto except for surgery.

Also, when the stenosis or the like occurs, even if the stenosis is opened by the balloon, bleeding may sometimes occur. In this case, it is difficult to deliver or provide a medicine or collagen to a bleeding portion in the blood vessel in order to stop bleeding.

Accordingly, one object of the invention is to provide a vascular therapy device for treatment easily in and around an area of a body cavity or blood vessel.

Another object of the invention is to provide a vascular therapy device as stated above, wherein the area can be treated from the inside of the body cavity or blood vessel without surgical treatment.

A further object of the invention is to provide a vascular therapy device as stated above, wherein the treatment can be made easily at the time of angioplasty.

Further objects and advantages of the invention will be apparent from the following description of the invention.

SUMMARY OF THE INVENTION

A vascular therapy device of the invention is formed of an elongated shaft having a distal end portion and proximal end portion, an inflatable balloon attached to a side portion of the distal end portion of the shaft so that when the balloon is inflated, a part of the distal end portion is biased to contact a wall where the shaft is inserted, a first path provided in the shaft and communicating with an inside of the balloon to inflate and deflate the balloon, and a second path provided inside the shaft and extending from the proximal end portion of the shaft to the distal end portion. The second path has an outlet at the distal end portion, so that when the balloon is inflated, the outlet faces and substantially contacts the wall to provide treatment at that contact portion through the second path and outlet.

Namely, in the invention, since the balloon is located at a side portion of the shaft, when the balloon is inflated, the distal end portion where the outlet is located is biased and contacts a portion, for example a wall of a blood vessel. Thus, a required treatment may be made at the contact portion through the second path and the outlet.

For example, a needle for injection may be inserted into the second path to inject a medicine in and around the contact portion. A capsules containing a medicine or collagen may be delivered to the contact portion. In this case, the distal end portion may be placed in that position for a while to properly treat that portion by the delivered medicine or collagen. Similarly, a radiation treatment material may be inserted into the second path to provide radiation therapy at the contact portion.

Further, a microwave antenna or RF (radio frequency) electrode may be introduced in and around the contact portion through the second path, similar to the needle. Also, the microwave antenna or RF electrode may be fixed around the outlet of the second path. The microwave antenna and RF electrode are used to heat the area where the microwave antenna and RF electrode contact. As a result, unnecessary or harmful cells may be destroyed or blood may be coagulated by the microwave antenna and RF electrode. Any other treatment may be made through the second path with the outlet.

Preferably, the vascular therapy device further includes means for defining a space at the distal end portion when the balloon is inflated. Namely, when the balloon is inflated, a liquid, i.e. blood, existed in a place where the vascular therapy device is disposed, may be blocked. However, the means for defining the space allows the liquid to pass through the distal end portion of the vascular therapy device. The means for defining the space may be a passage formed between the balloon and the shaft. The balloon may have projections with a space therebetween to allow the liquid to pass through the space.

Since the space is formed, when the balloon is inflated, the liquid or blood can flow through the vascular therapy device. Thus, the treatment by the vascular therapy device can be made for a long period of time.

In the vascular therapy device, the outlet may be located at a side wall of the distal end portion, or at a front end of the distal end portion.

In case the vascular therapy device is delivered through a guide wire, a guide wire passageway is provided in at least the distal end portion of the elongated shaft.

DETAILED DESCRIPTION OF PREFERRED EMBODIMENTS

Hereunder, embodiments of the invention will be explained with reference to the accompanying drawings. In explaining the embodiments, the constituents which are the same as in the first embodiment are designated by the same numeral references in other embodiments, so that the explanations thereof are omitted.

Figure 1:
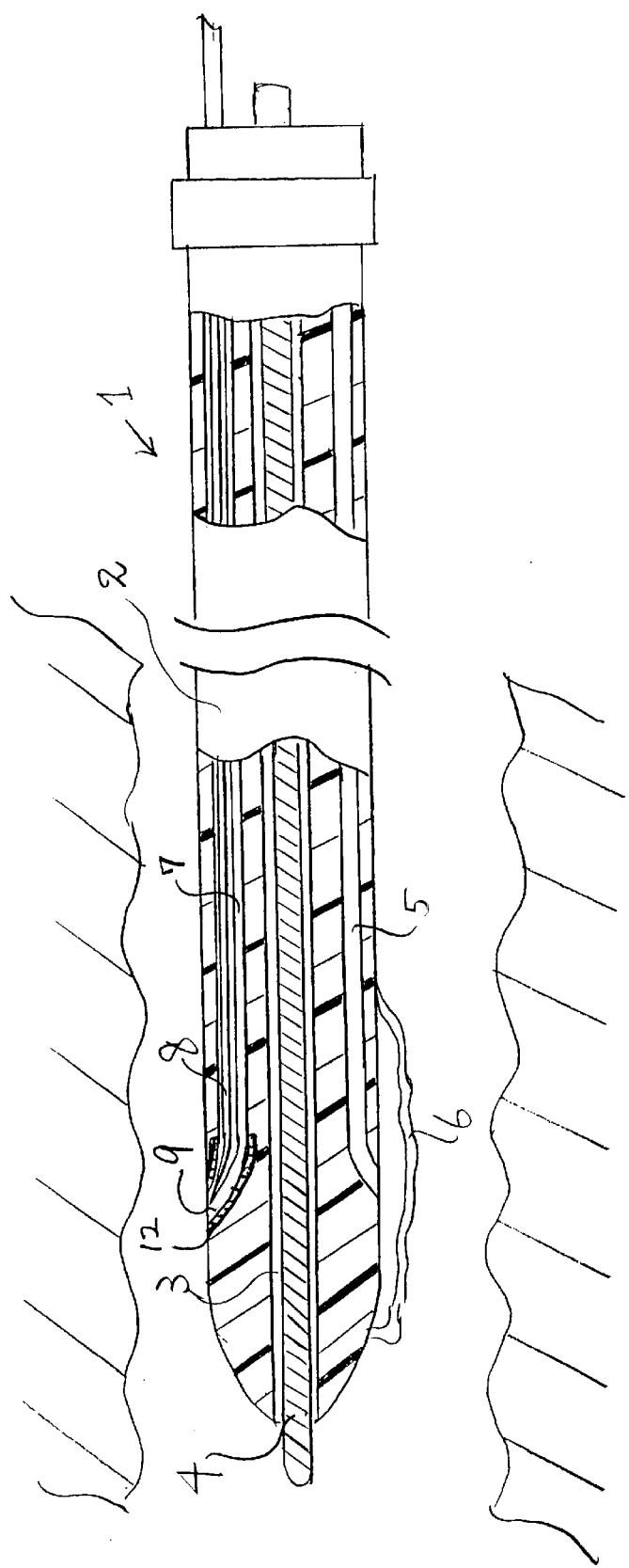
FIG. 1 is a partially sectional explanatory view of a first embodiment of a vascular therapy device of the invention, showing a condition that the vascular therapy device is placed inside a body cavity or blood vessel and a balloon attached to the vascular therapy device is deflated.

FIG. 1 is a partially sectional explanatory view of a first embodiment of a vascular therapy device of the invention, wherein the vascular therapy device is placed inside a blood vessel.

As shown in FIG. 1, a vascular therapy device 1 of the first embodiment is basically formed of an elongated shaft 2, and a balloon 6 attached to the shaft 2. The shaft 2 includes a guide wire passageway 3 through which a guide wire 4 passes, a first path 5 for introducing fluid into the balloon 6 attached to the shaft 2 so as to inflate or deflate the balloon 6, and a passageway or second path 7 for delivering a treating device or material, e.g. elongated needle 8, to a desired location in the body cavity or the blood vessel. A middle part of the balloon 6 is not completely bonded to the shaft 5 to form a space 6' between the balloon 6 and the shaft 5.

A distal end of the passageway 7 is opened to define an outlet or side hole 9 located at a distal end portion of the vascular therapy device 1, and a metal sleeve or cannula 12 is disposed in and around the outlet 9. As shown in FIG. 1, the side hole 9 is located on a side of the vascular therapy device 1 opposite to a side where the balloon 6 is attached.

In use, as in the conventional catheter system, the guide wire 4 is preliminary placed inside the blood vessel, and then the vascular therapy device 1 as structured above is introduced over the guide wire 4 to be located inside the blood vessel for treating a lesion or the like as shown in FIG. 1. While the vascular therapy device 1 is being delivered to a desired location, the balloon 6 is not inflated as shown in FIG. 1.

Figure 2:
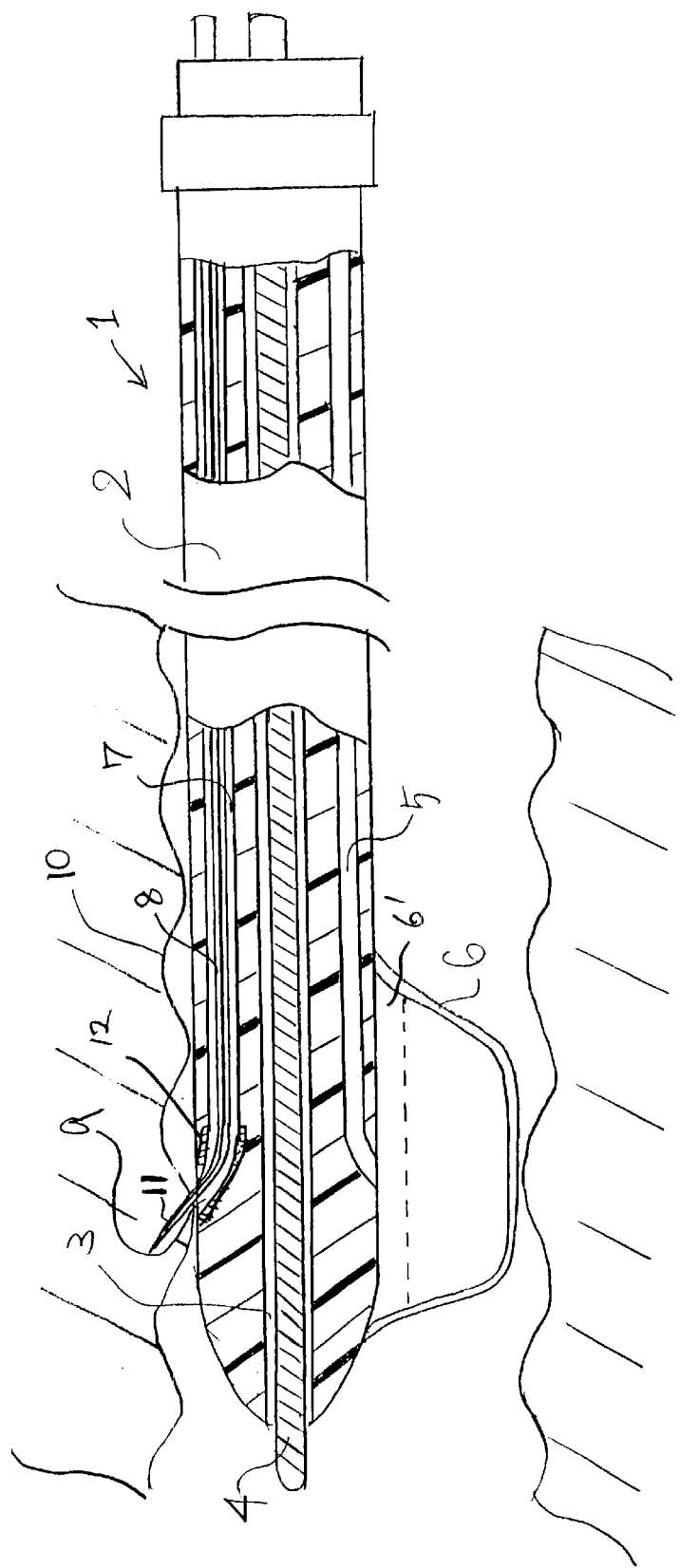
FIG. 2 is a partially sectional explanatory view of the first embodiment of the vascular therapy device, showing a condition that the balloon is inflated and a needle is delivered to a desired location for injection.

After the vascular therapy device 1 is delivered to the desired location in the blood vessel, a fluid is introduced into the first path 5 to inflate the balloon 6. When the balloon 6 is inflated, the side of the distal end portion of the vascular therapy device 1 where the side hole 9 is located is pushed toward a wall 10 of the blood vessel to abut against the wall 10 as shown in FIG. 2. At this time, the space 6' is established between the balloon 6 and the shaft 5 to allow the blood to pass through the space 6'. Thus, the blood flowing in the blood vessel is not blocked by the balloon 6.

Then, the elongated needle 8 located inside the passageway 7 is pushed to allow the distal end 11 of the needle 8 to bend and project outside the passageway 7 and to enter into the wall 10 of the blood vessel. The metal sleeve 12 allows the needle 8 to bend along the passageway 7. Thereafter, a conventional syringe and a piston (not shown) attached to the proximal end of the needle 8 are manipulated to inject a medicine for treatment. Accordingly, a necessary treatment in the portion of the blood vessel can be made.

In this embodiment, when the vascular therapy device 1 is delivered, the needle 8 is placed in the passageway 7 though the distal end 11 of the needle is located inside the passageway 7. However, the vascular therapy device 1 without the needle therein may be delivered through the blood vessel, and after the device 1 is delivered to the desired location, the needle 8 may be entered into the passageway 7.

Figure 3:
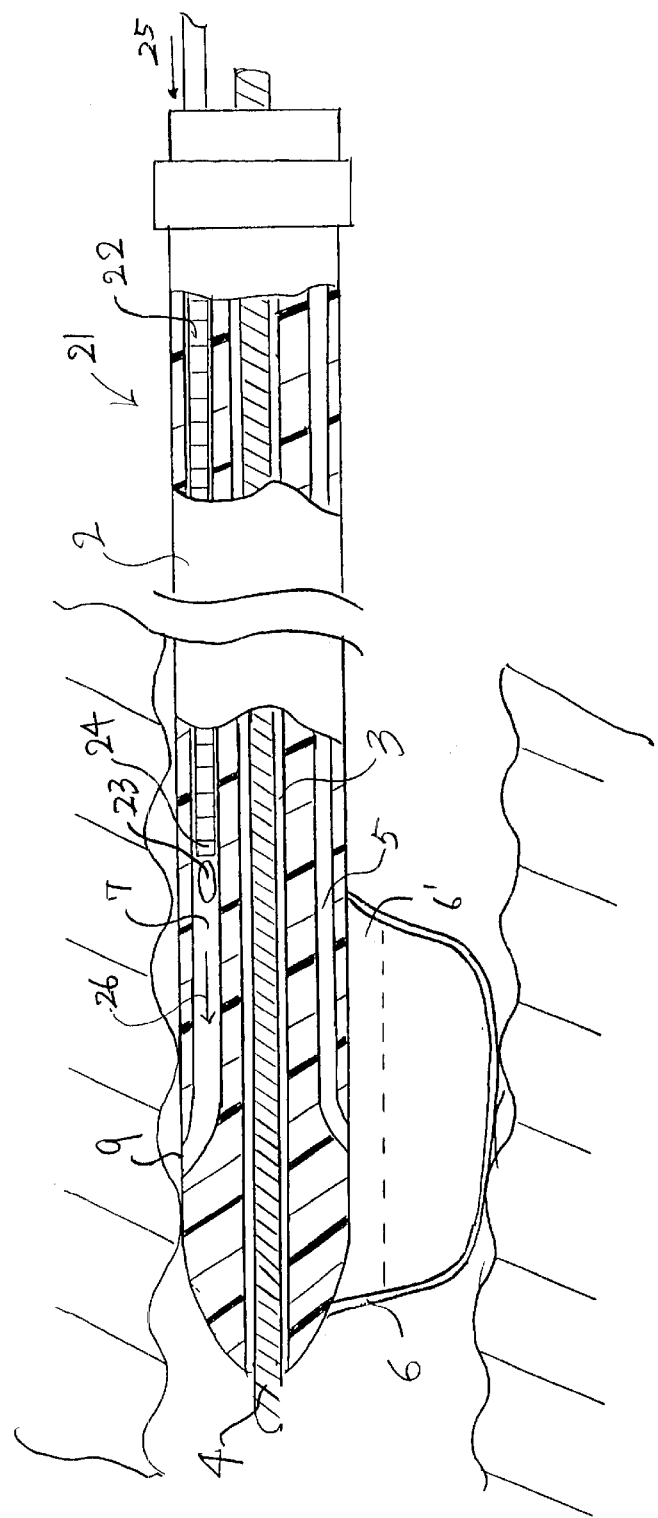
FIG. 3 is a partially sectional explanatory view of a second embodiment of the vascular therapy device of the invention, showing a condition that a capsule is being delivered inside the vascular therapy device.

FIG. 3 is a partly sectional explanatory view of a second embodiment of the vascular therapy device of the invention. In the second embodiment, instead of the elongated needle 8 in the first embodiment, a vascular therapy device 21 provided with a pusher 22 is used. The pusher 22 has an elongated rod shape and is placed inside the passageway 7. Also, a capsule 23 including collagen or medicine is disposed at a distal end 24 of the pusher 22 in the passageway 7.

Figure 4:
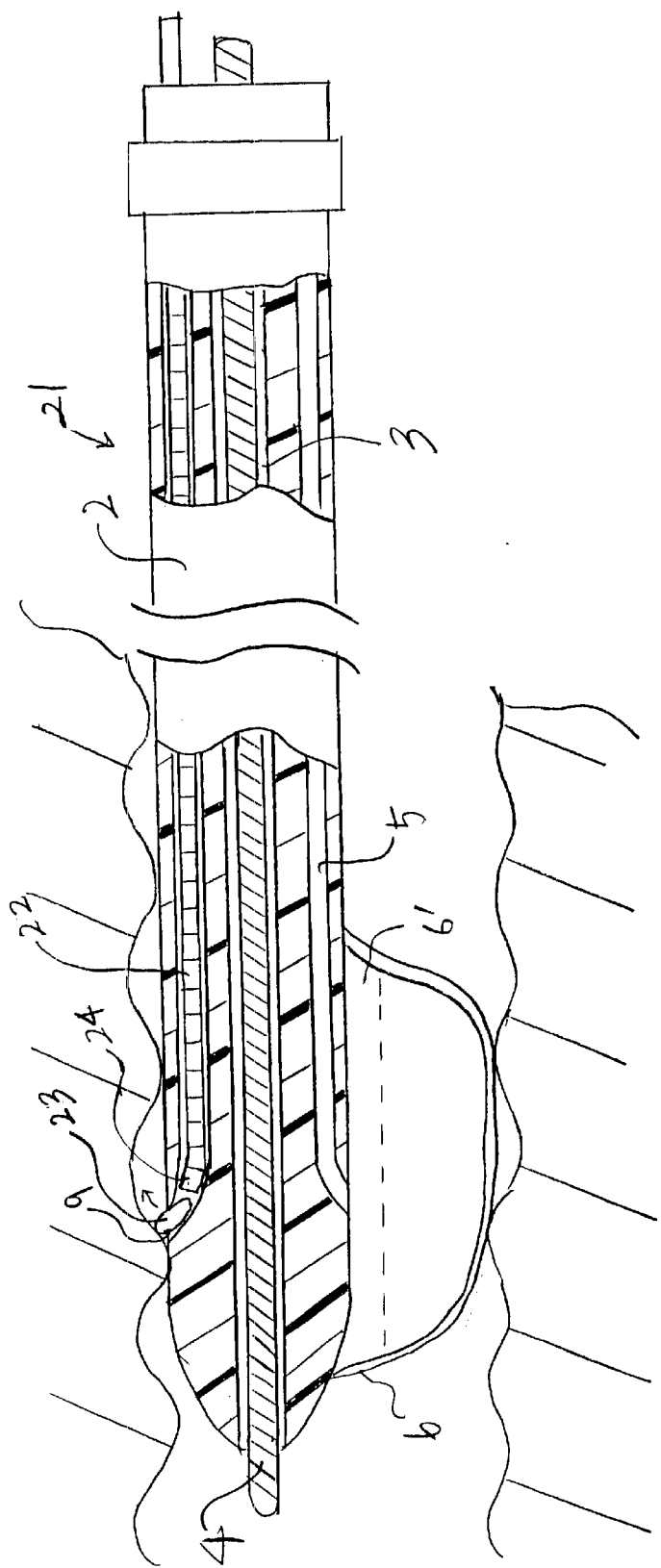
FIG. 4 is a partially sectional explanatory view of the second embodiment, showing a condition that the capsule is pushed out from a side hole provided in the vascular therapy device.

In use, the vascular therapy device 21 is delivered into the desired location and the balloon 6 is inflated, as in the first embodiment. Then, the capsule 23 is pushed by the pusher 20 inside the passageway 7 in a direction shown by arrows 25, 26 in FIG. 3. When the capsule 23 is pushed to pass through the side hole 9 as shown in FIG. 4, the capsule 23 including the collagen or medicine is disposed in that portion for a while to treat the portion by the medicine or collagen by leaving the vascular therapy device 21 at that position. Since the blood vessel is not blocked by the space 6', the vascular therapy device 21 can be left in the blood vessel without trouble.

Figure 5:
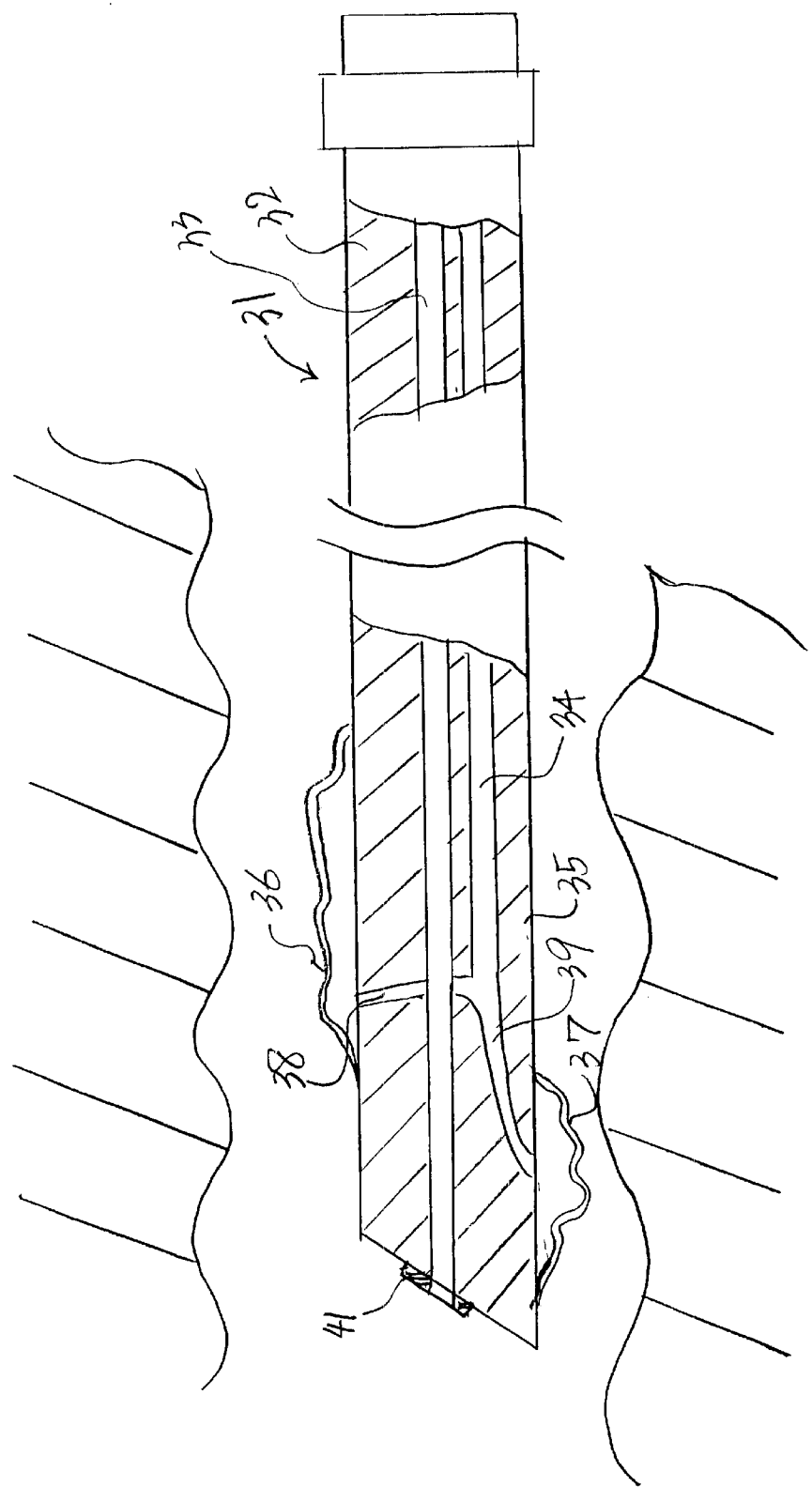
FIG. 5 is a partially sectional explanatory view of a third embodiment of the vascular therapy device of the invention, wherein a pair of balloons provided on the vascular therapy device is deflated.

FIG. 5 is a partly sectional explanatory view of a third embodiment of a vascular therapy device 31 of the invention, wherein the vascular therapy device has a distal end having an end hole instead of a side hole in the shaft.

In the third embodiment, the vascular therapy device 31 is basically formed of an elongated shaft member 32 having a passageway 33 and a path 34 bifurcated at a distal end portion 35 of the vascular therapy device 31. Also, a pair of balloons 36, 37 is attached to the distal end portion 35 of the vascular therapy device 31 to communicate with bifurcated portions 38, 39 of the path 34.

The balloons 36, 37 are axially displaced from each other. Namely, the balloon 36 is located at one side of a front end, while the balloon 37 is located at the other side and spaced slightly away from the balloon 36 as shown in FIG. 5. The passageway 33 extends axially throughout the entire length of the vascular therapy device 31, and can be used for delivering a needle, a capsule or the like as in the first and second embodiments. The path 34 is used for introducing a fluid to the balloons 36, 37 to inflate and deflate the same. In FIG. 5, the balloons 36, 37 are deflated.

The vascular therapy device 31, also, includes an RF (radio frequency) electrode 41 around an outlet of the passageway 33, and a lead wire (not shown) extending from the RF electrode 41 to the proximal end of the vascular therapy device 31. The RF electrode 41 operates to heat the area where the electrode contacts, to thereby destroy the cell or coagulate blood. Instead of the RF electrode, a microwave antenna may be attached to heat the area as in the RF electrode.

In use, as in the first and second embodiments, the vascular therapy device 31 is delivered to a desired location, i.e. portion here a treatment is required, in a patient's body cavity as shown in FIG. 5.

Figure 6:
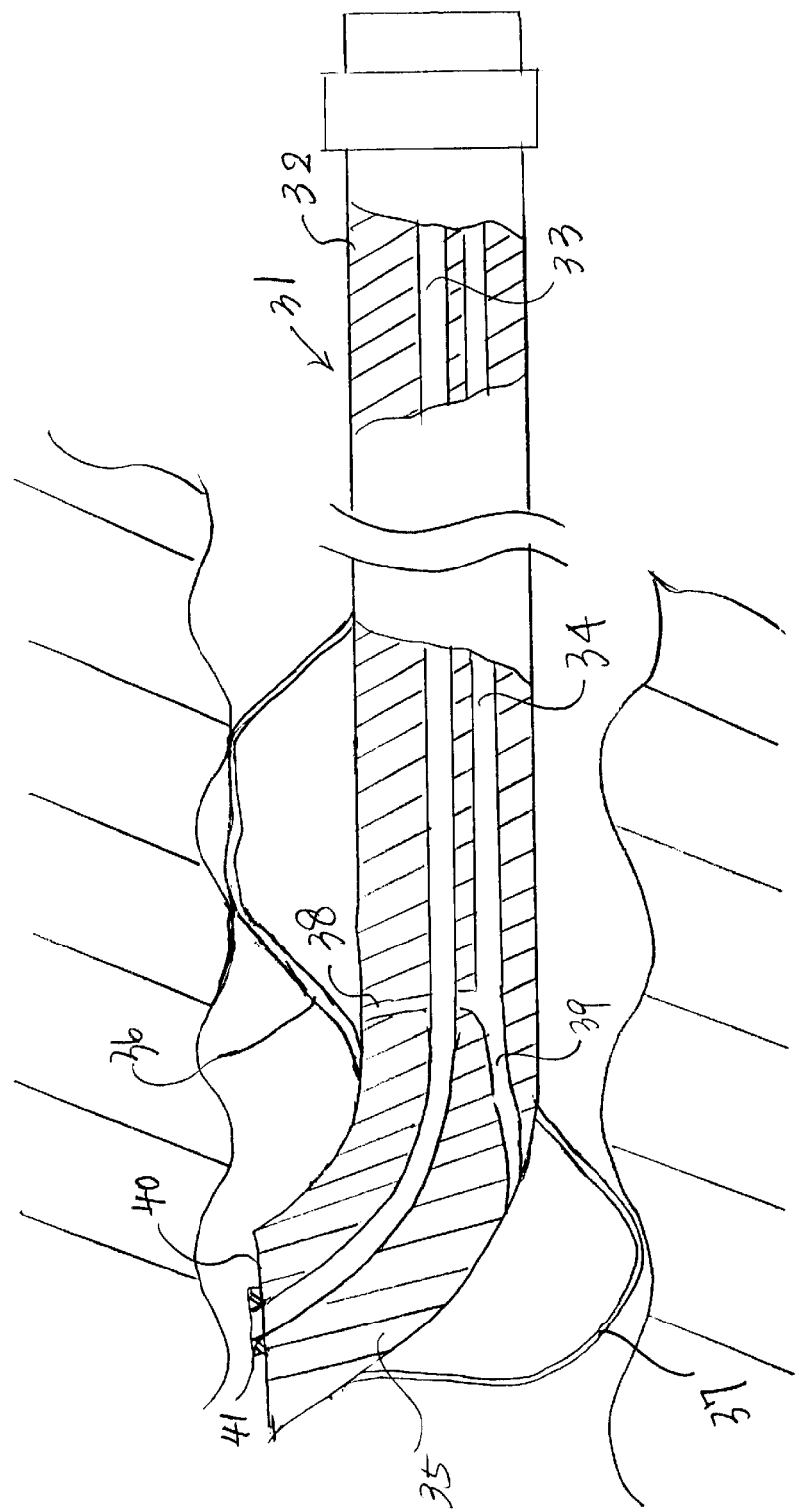
FIG. 6 is a partially sectional explanatory view of the third embodiment, wherein the balloons are inflated to bend a distal end of the device.

Then, a fluid is introduced into the path 34 to inflate the balloons 36, 37. Since the balloons are laterally displaced, when the balloons 36, 37 are inflated, the front end 35 of the vascular therapy device 31 is bent toward an upper side in FIG. 6, so that a distal end 40 of the vascular therapy device 31 faces a wall portion of the body cavity.

After the distal end 40 faces the wall of the body cavity, as in the first or second embodiment, an elongated needle for injecting a medicine, capsule or collagen can be delivered through the passageway 33 to be located on the wall portion of the body cavity. If required, the front end portion 35 is bent in that position for a while to treat that portion properly.

Since the vascular therapy device 31 includes the RF electrode 41, it can be used as an RF catheter to treat a wall of the vascular system. When the RF electrode 41 is activated, the RF electrode 41 emits radioactive frequency to heat or destroy the undesirable or diseased cells in the wall of the vessel.

Although the vascular therapy device is used in the blood vessel of a patient in the embodiments explained in the invention, the vascular therapy device of the invention can be used in any body cavities of the patient.

In the present invention, the area around the body cavity or blood vessel can be treated through the inside thereof without surgical treatment. Thus, the treatment can be made without risk and burden to the patient.

While the invention has been explained with reference to the specific embodiments of the invention, the explanation is illustrative and the invention is limited only by the appended claims.

What is claimed is:

1. A vascular therapy device, comprising:
   an elongated shaft having a distal end portion with a front end and a proximal end portion,
   a first inflatable balloon attached to the distal end portion of the shaft at one side of the shaft and a second inflatable balloon located at the other side thereof and spaced slightly away from the first balloon so that when the first and second balloons are inflated, the front end of the shaft is biased to face and contact a wall where the shaft is inserted,
   a first path provided in the shaft and communicating with the first and second balloons to inflate and deflate the balloons, and
   a second path provided inside the shaft and extending from the proximal end portion of the shaft to the distal end portion, said second path having an outlet in the front end of the distal end portion so that when the balloons are inflated, the outlet faces and substantially contacts the wall to provide a treatment through the second path and outlet.

2. A vascular therapy device according to claim 1, further comprising means for defining a space at the distal end portion so that when the balloons are inflated, proximal and distal sides of the first balloon in a longitudinal direction of the shaft can partly communicate through the space at the distal end portion.

3. A vascular therapy device according to claim 2, wherein said means for defining the space is a passage formed between the first balloon and the shaft.

4. A vascular therapy device according to claim 1, further comprising a guide wire passageway provided in at least the distal end portion of the elongated shaft to deliver the shaft along a guide wire passing through the guide wire passageway.

5. A vascular therapy device according to claim 1, further comprising an elongated needle to be disposed in the second path so that a distal end of the elongated needle is projected from the outlet for treatment.

6. A vascular therapy device according to claim 1, further comprising an elongated bar member to be disposed in the second path so that a material placed at a distal end of the bar member is delivered outside the outlet through the second path.

7. A vascular therapy device according to claim 1, further comprising a heating member formed around the outlet to heat a portion around the heating member, said heating member being selected from a group consisting of a radio frequency electrode and microwave antenna.

8. A vascular therapy device, comprising:
   an elongated shaft having a distal end portion and a proximal end portion,
   an inflatable balloon attached to a side portion of the distal end portion of the shaft so that when the balloon is inflated, a part of the distal end portion is biased to contact a wall where the shaft is inserted,
   a passage formed between the balloon and the shaft so that when the balloon is inflated, outer portions on two sides of the balloon in a longitudinal direction of the shaft can communicate through the passage at the distal end portion,
   a first path provided in the shaft and communicating with an inside of the balloon to inflate and deflate the balloon, and
   a second path provided inside the shaft and extending from the proximal end portion of the shaft to the distal end portion, said second path having an outlet at the distal end portion so that when the balloon is inflated, the outlet faces and substantially contacts the wall to provide a treatment through the second path and outlet.

9. A vascular therapy device according to claim 8, further comprising an elongated needle to be disposed in the second path so that a distal end of the elongated needle is projected from the outlet for treatment.

10. A vascular therapy device according to claim 8, further comprising an elongated bar member to be disposed in the second path so that a material placed at a distal end of the bar member is delivered outside the outlet through the second path.

11. A vascular therapy device according to claim 8, wherein said outlet is located at a portion away from the balloon.

12. A vascular therapy device according to claim 11, wherein said outlet is located at a side wall of the distal end portion.

13. A vascular therapy device according to claim 11, wherein said outlet is located at a front end of the distal end portion.

14. A vascular therapy device according to claim 9, further comprising a metal sleeve formed in the second path around the outlet so that the needle is bent thereat to project from the outlet.

* * * * *